US00PP28732P3

(12) United States Plant Patent
Yamada

(10) Patent No.: US PP28,732 P3
(45) Date of Patent: Dec. 5, 2017

(54) ***CATHARANTHUS* PLANT NAMED 'SUNCATHAMIHO'**

(50) Latin Name: *Catharanthus roseus*
Varietal Denomination: Suncathamiho

(71) Applicant: SUNTORY FLOWERS LIMITED, Tokyo (JP)

(72) Inventor: Masahiro Yamada, Kanagawa (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 386 days.

(21) Appl. No.: 14/121,585

(22) Filed: Sep. 19, 2014

(65) Prior Publication Data

US 2015/0089699 P1 Mar. 26, 2015

Related U.S. Application Data

(60) Provisional application No. 61/960,539, filed on Sep. 20, 2013.

(51) Int. Cl.
*A01H 5/02* (2006.01)

(52) U.S. Cl.
USPC ..... Plt./263.1
CPC ..... *A01H 5/02* (2013.01)

(58) Field of Classification Search
USPC ..... Plt./263.1, 226
CPC ..... A01H 5/02; A01H 5/00
See application file for complete search history.

(56) References Cited

U.S. PATENT DOCUMENTS

PP20,289 P2 * 9/2009 Saul ..... A01H 5/02
Plt./263.1

OTHER PUBLICATIONS

"2012 Spring-Summer gardening catalog," Daiichi Engei Co., Ltd., Oct. 2011, pp. 22-23.
Registration No. 22599, Registration date Jul. 29, 2013, Suntory Flowers Company, 1 page.

* cited by examiner

*Primary Examiner* — Kent L Bell
(74) *Attorney, Agent, or Firm* — Kilpatrick Townsend & Stockton LLP

(57) ABSTRACT

Disclosed herein is a new and distinct variety of *Catharanthus* plant having vigorous, upright plant characteristics, abundant branching, especially basally branching, developed from the base of the plant throughout the growing season, great profusion of single, pale pink flowers, the whole bush remaining in bloom for a considerable period of time and deeply bitten petals, shaped of hastate, incurvated.

2 Drawing Sheets

Botanical designation: *Catharanthus roseus.*
Cultivar denomination: 'Suncathamiho'.

BACKGROUND OF THE INVENTION

The present invention relates to a new and distinct variety of *Catharanthus* plant, which is hereinafter referred to by the name of 'Suncathamiho'.

*Catharanthus roseus*, which is also known as *Vinca rosea*, is a very popular plant that is used for flower bedding and potting in the summer and autumn season.

The purpose of this invention is to obtain a new *Catharanthus* cultivar having vigorous, upright plant characteristics, abundant branching, especially basally branching, developed from the base of the plant throughout the growing season, great profusion of single, pale pink flowers, the whole bush remaining in bloom for a considerable period of time and irregularity incised petals, shaped of hastate, incurvated.

The new *Catharanthus* plant was originated from a cross-pollination of the female parent 'MC21-15' and the male parent 'MC21-P-2'. The female parent 'MC21-15' (unpatented) used in the crossing of 'Suncathamiho' is a strain of applicant's breeding lines (i.e., proprietary *Catharanthus roseus* selection), having white petals, and the male parent 'MC21-P-2' (unpatented) used in the crossing of 'Suncathamiho' is a strain of applicant's breeding lines (i.e., proprietary *Catharanthus roseus* selection), having rotund petal shape. The cross-pollination was conducted in August, 2011 at Yame-gun, Fukuoka, Japan.

In February 2012, the seedlings obtained by the crossing were planted in field, and some seedlings were selected in view of growth habit, flower size and color thereof. In August 2012, the stem tip culturing was carried out, and then the propagation was started.

In July 2013, the cultivation of the seedlings was repeated. The botanical characteristics of that plant were then examined, using similar varieties 'Milk crown blushing pink' and 'Daiichi-MC21-25' for comparison. As a result, it was concluded that this *Catharanthus* plant is distinguishable from any other variety, whose existence is currently known, and is uniform and stable in its characteristics.

The new variety of *Catharanthus roseus* plant is named 'Suncathamiho'.

SUMMARY OF THE INVENTION

This new variety is unlike any *Catharanthus* plants commercially available as evidenced by the following unique combinations of characteristics.

1. Vigorous, upright plant characteristics.
2. Abundant branching, especially basally branching, developed from the base of the plant throughout the growing season.
3. Great profusion of single, pale pink flowers, the whole bush remaining in bloom for a considerable period of time.
4. irregularly incised petals, shaped of hastate, incurvated.

The new variety 'Suncathamiho' differs from the similar variety 'Milk crown blushing pink', which was applied for Japanese plant variety protection (the application number: 23662; the application date: 2009 Apr. 2; the registration number 21019; the registration date: 2011 Sep. 8), in the following points.

1. The petals overlap of 'Suncathamiho' is contacting. That of 'Milk crown blushing pink' is separating.
2. The secondary color of surface of corolla lobe of 'Suncathamiho' is brilliant purplish pink (RHS 62B). That of 'Milk crown blushing pink' is RED-PURPLE (RHS 61C).

The new variety 'Suncathamiho' differs from the similar variety 'Daiichi-MC21-25', which was applied for Japanese plant variety protection (the application number: 26287; the application date: 2011 Sep. 8; the registration number 22599; the registration date: 2013 Jul. 29), in the following points.

1. The main color of surface of corolla lobe of 'Suncathamiho' is pale pink (RHS 62D). That of 'MC21-25' is purple (RHS N80B).
2. The leaf size (L×W) of 'Suncathamiho' is 51 mm×23.3 mm. The leaf size of 'Daiichi-MC21-25' is 60 mm×33 mm.
3. The flower eye of 'Suncathamiho' is absent. That of 'Daiichi-MC21-25' is present.

This new variety of *Catharanthus* plant 'Suncathamiho' was asexially reproduced by the use of cuttings at Higashiomi, Shiga, Japan, and homogeneity and stability thereof were confirmed. The instant plant retains its distinctive characteristics and produces true to type in successive generations.

BRIEF DESCRIPTION OF THE PHOTOGRAPHS

The depicted plants had been reproduced by the use of cuttings and were photographed during October 2013 while growing outdoors in wall pots with about 15 cm of container size at an age of approximately 6 months.

The second sheet is a photograph of a typical plant of the new variety of *Catharanthus* plant 'Suncathamiho' while growing in a pot.

The first sheet is a photograph of a close view of flowers of the new variety of *Catharanthus* plant 'Suncathamiho'.

DETAILED BOTANICAL DESCRIPTION

In October 2013, the cultivation of the seedlings was repeated at Higashiomi, Shiga, Japan. The average day temperature was about 25° C., and the average night temperature was about 15° C. The plants were grown under natural sunlight. The number of days to flowering (response time) was about 3 to 4 weeks. The keeping quality was about 180 days. The plants had temperature resistance to about 5° C. (the lowest temperature) and about 35 to 40° C. (the highest temperature). Further, the plants had the same tolerance to pests and pathogens as a typical *Catharanthus* plant.

For the parentage information: The female parent 'MC21-15' (unpatented) used in the crossing of 'Suncathamiho' is a strain of applicant's breeding lines (i.e., proprietary *Catharanthus roseus* selection), having white petals, and the male parent 'MC21-P-2' (unpatented) used in the crossing of 'Suncathamiho' is a strain of applicant's breeding lines (i.e., proprietary *Catharanthus roseus* selection), having rotund petal shape.

For the propagation information: the new cultivar was propagated by cutting; the number of days to initiate roots during the summer was about two weeks; approximate soil and/or air temperature during the summer was around 30° C.; the number of days to initiate roots during the winter was about three weeks; approximate soil and/or air temperature during the winter was around 25° C.; the number of days to produce a rooted young plant during the summer was about five weeks; the number of days to produce a rooted young plant during the winter was about six weeks; root density was moderate; root branching was free; root color was white; and root texture was fibrous.

The botanical characteristics of the new and distinct variety of *Catharanthus* plant named 'Suncathamiho' at an age of approximately 4 months are shown in the following Table. In the following description, the color-coding is in accordance with the Horticultural Colour Chart of The Royal Horticultural Society, London, England (R.H.S. Colour Chart The 5th edition 2007).

PLANT VARIETY DESCRIPTION

| CHARACTERISTIC | APPLICATION VARIETY Suncathamiho |
|---|---|
| ANNUAL, BIENNIAL or PERENNIAL? | Grown as annual. |
| TYPE OF PLANT: i.e., TREE, SHRUB, SUBSHRUB, VINE, CUT FLOWER, POTTED PLANT | Potted plant |
| APPROPRIATE CONTAINERS +/or CROPPING SYSTEM | Ideal for pots, hanging baskets. |
| GROWTH HABIT | Upright |
| PLANT HEIGHT | About 25.0 cm |
| PLANT DIAMETER OR AREA OF SPREAD | About 25.0 cm |
| PLANT VIGOR | Vigorous |
| BRANCHING HABIT | Freely branching |
| BASAL BRANCHING? | Present |
| PINCHING REQUIRED? | Not required. |
| NUMBER OF LATERAL BRANCHES | About 5 |
| NUMBER OF SECONDARY LATERAL BRANCHES | About 4 |
| LATERAL BRANCH LENGTH | About 17.3 cm |
| LATERAL BRANCH DIAMETER | About 3.9 mm |
| INTERNODE LENGTH | About 19.9 mm |
| STEM ASPECT | Upright to outward |
| STEM COLOR (and bark color, if applicable) | RHS Near 144D |
| STEM COLOR (if any) | RHS Near 51D |
| STEM PUBESCENCE? | Absent |
| OTHER PLANT/STEM CHARACTERISTICS | — |
| LEAF ARRANGEMENT | Opposite |
| COMPOUND OR SIMPLE? | Simple |
| QUANTITY OF LEAVES PER LATERAL BRANCH | About 13 |
| LEAF (LEAFLET) SHAPE | Elliptic |
| LEAF (LEAFLET) TIP | Acute |
| LEAF (LEAFLET) BASE | Obtuse |
| LEAF LENGTH | About 51.0 mm |
| LEAF WIDTH | About 23.3 mm |
| LEAF THICKNESS | About 0.3 mm |
| LEAF (LEAFLET) TEXTURE | Pubescent, both sides |
| LEAF PUBESCENCE? WHICH SIDE? | Present |
| LEAF (LEAFLET) MARGIN | Entire |
| VENATION PATTERN | Reticulate venation |

-continued

PLANT VARIETY DESCRIPTION

| CHARACTERISTIC | APPLICATION VARIETY Suncathamiho |
|---|---|
| LEAF COLOR, YOUNG, UPPER SIDE | RHS Near 137B |
| LEAF COLOR, YOUNG, UNDER SIDE | RHS Near 137D |
| LEAF COLOR, MATURE, UPPER SIDE | RHS Near 143A to 143C |
| LEAF COLOR, MATURE, UNDER SIDE | RHS Near 137B |
| VENATION COLOR, UPPER SIDE | RHS Near 137D |
| VENATION COLOR, UNDER SIDE | RHS Near 142D |
| VARIEGATION? | Absent |
| PETIOLE? | Present |
| PETIOLE LENGTH | About 9.1 mm |
| PETIOLE DIAMETER | About 1.6 mm |
| PETIOLE TEXTURE | Pubescent |
| PETIOLE COLOR | RHS Near 145B |
| OTHER FOLIAGE CHARACTERISTICS | — |
| FLOWER ARRANGEMENT | Borne in upper leaf axils. |
| INFLORESCENCE TYPE OR FORM (if applicable) | Solitary |
| QUANTITY OF FLOWERS PER PLANT | About 50 |
| FLOWER TYPE or FORM | Single |
| FLOWERING HABIT | Continuously |
| NATURAL FLOWERING SEASON | Early summer to late autumn |
| TIME TO FLOWER OR RESPONSE TIME | About 2~3 weeks |
| FRAGRANCE | Absent |
| FLOWER BUD LENGTH | About 35.4 mm |
| FLOWER BUD DIAMETER | About 5.9 mm |
| FLOWER BUD SHAPE | Clavate |
| FLOWER BUD COLOR | RHS Near 19C |
| FLOWER ASPECT; i.e., UPRIGHT, OUTWARD, DROOPING, etc. | Upright |
| FLOWER PARACOROLLA | Absent |
| FLOWER DIAMETER | About 36.7 mm |
| FLOWER DEPTH (HEIGHT) | About 38.3 mm |
| FLOWER LONGEVITY ON PLANT | About 2~3 days |
| PERSISTENT OR SELF-CLEANING? | Not persistent. |
| PETAL TEXTURE, UPPER SURFACE | Smooth |
| PETAL TEXTURE, LOWER SURFACE | Smooth |
| TUBE TEXTURE | Smooth, slightly pubescent |
| PETAL ARRANGEMENT | Free |
| PETAL NUMBER | 5 |
| PETALS FUSED? | Fused |
| PETAL SHAPE | Hastate |
| PETAL MARGIN | Absent |
| PETAL SHAPE, SYMMETRY OR ASYMMETRY? | Asymmetry |
| PETAL TIP | irregularly incised |
| PETAL BASE | Fused |
| PETAL LENGTH | About 20.8 mm |
| PETAL WIDTH | About 12.1 mm |
| PETAL COLOR, WHEN OPENING, UPPER SIDE | RHS Near 62D |
| PETAL COLOR, WHEN OPENING, LOWER SIDE | RHS Near 65D |
| PETAL COLOR, FULLY OPENED, UPPER SIDE | RHS Near 62D |
| PETAL COLOR, FULLY OPENED, LOWER SIDE | RHS Near 65D |
| PETAL SECONDARY COLOR, UPPER SIDE | RHS Near 62B |
| DISTRIBUTION OF PETAL SECONDARY COLOR, UPPER SIDE | Gradating from base to mid-section. |
| RATE OF PETAL SECONDARY COLOR, UPPER SIDE | Few |
| FLOWER EYE | Absent |
| FLOWER EYE DIAMETER | — |

-continued

PLANT VARIETY DESCRIPTION

| CHARACTERISTIC | APPLICATION VARIETY Suncathamiho |
|---|---|
| FLOWER EYE COLOR | — |
| RECEPTACLE | Present |
| RECEPTACLE COLOR | RHS Near 3C |
| TUBE DIAMETER | About 1.8 mm |
| TUBE LENGTH | About 26.2 mm |
| THROAT COLOR (inside) | RHS Near 145C |
| TUBE COLOR (outside) | RHS Near 145A to 145B Base: with anthocyanin pigmentation |
| SEPAL ARRANGEMENT | Single whorl |
| NUMBER OF SEPALS | 5 |
| SEPAL SHAPE | Linear-triangular |
| SEPAL MARGIN | Entire |
| SEPAL TIP | Acute |
| SEPAL BASE | Fused |
| SEPAL LENGTH | About 3.3 mm |
| SEPAL WIDTH | About 1.1 mm |
| SEPAL COLOR, IMMATURE, UPPER SIDE | RHS Near 144A |
| SEPAL COLOR, IMMATURE, UNDER SIDE | RHS Near 144A |
| SEPAL COLOR, MATURE, UPPER SIDE | RHS Near 144A |
| SEPAL COLOR, MATURE, UNDER SIDE | RHS Near 144A |
| CALYX SHAPE | Star shape |
| CALYX LENGTH | About 4.5 mm |
| CALYX DIAMETER | About 5.1 mm |
| PEDUNCLE LENGTH | About 3.5 mm |
| PEDUNCLE DIAMETER | About 1.6 mm |
| PEDUNCLE ANGLE | Upright |
| PEDUNCLE TEXTURE | Smooth |
| PEDUNCLE COLOR | RHS Near 144C |
| STAMEN NUMBER | 5 |
| STAMEN LENGTH | About 2.6 mm |
| ANTHER SHAPE | Narrow elliptic |
| ANTHER SIZE (L) | About 2.5 mm |
| ANTHER SIZE (W) | About 1.1 mm |
| ANTHER COLOR | RHS Near 8D |
| AMOUNT OF POLLEN | Few |
| POLLEN COLOR | RHS Near 4D |
| PISTIL NUMBER | 1 |
| PISTIL LENGTH | About 17.7 mm |
| STIGMA SHAPE | Transversely ellipsoidal |
| STIGMA COLOR | RHS Near 145A |
| STYLE COLOR | RHS Near 145C |
| OVARY COLOR | RHS Near 145B |
| OTHER FLOWER CHARACTERISTICS | — |
| QUANTITY OF SEEDS | Seed production has not been observed. |
| ROOT STRUCTURES such as BULBS, CORMS or RHIZOMES? | Fibrous root |
| LOW TEMPERATURE TOLERANCE | Around 5° C. |
| HIGH TEMPERATURE TOLERANCE | Around 35° C.~40° C. |
| DISEASE RESISTANCE AND/OR SUSCEPTIBILITY | Normal |
| RESISTANCE OF PESTS AND/OR SUSCEPTIBILITY | Normal |

This new variety of *Catharanthus* plant having the above botanical characteristics is suitable for flower bedding and potting, particularly in hanging pots or planters.

What is claimed:

1. A new and distinct variety of *Catharanthus* plant named 'Suncathamiho', substantially as herein illustrated and described.

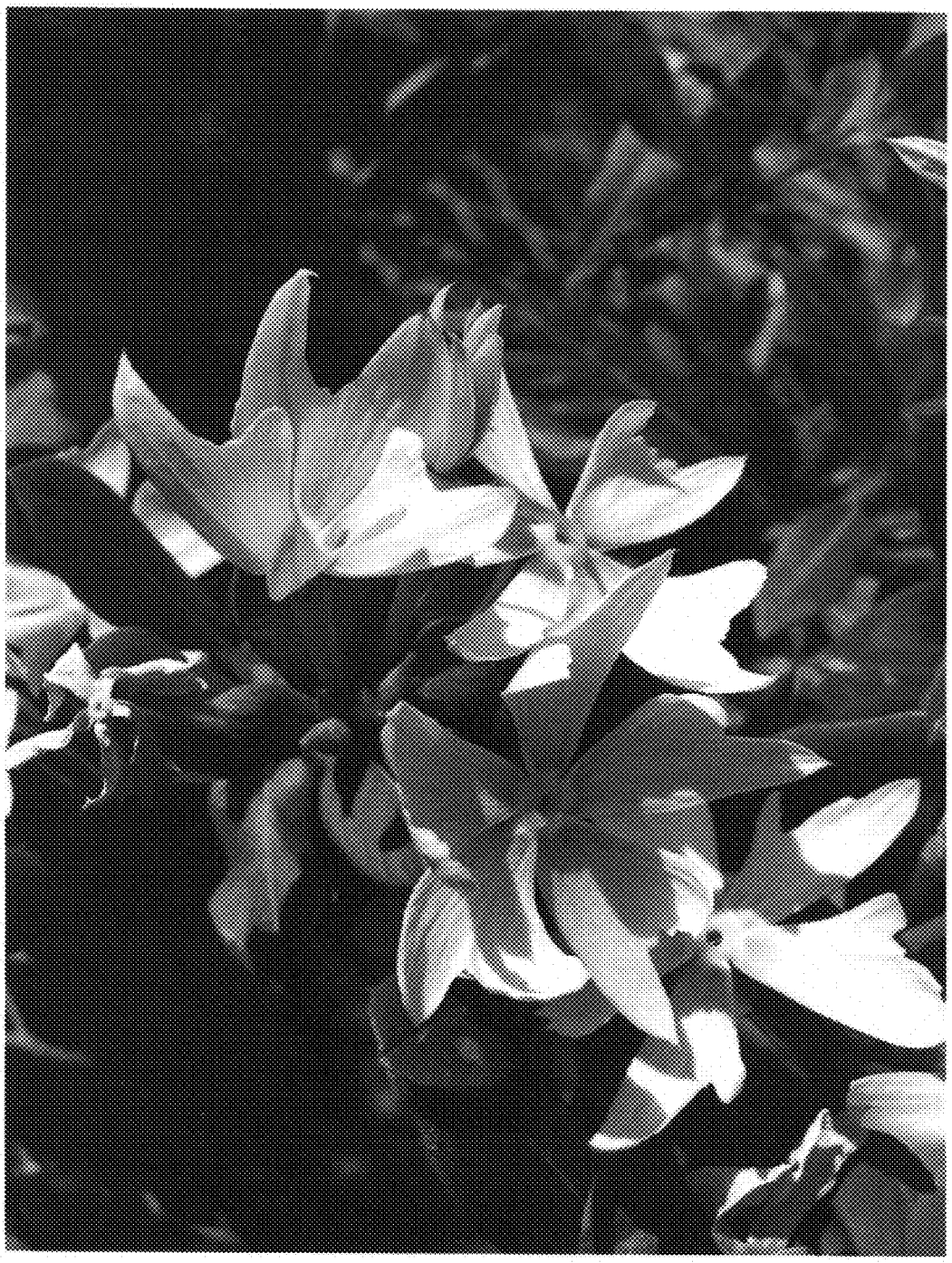

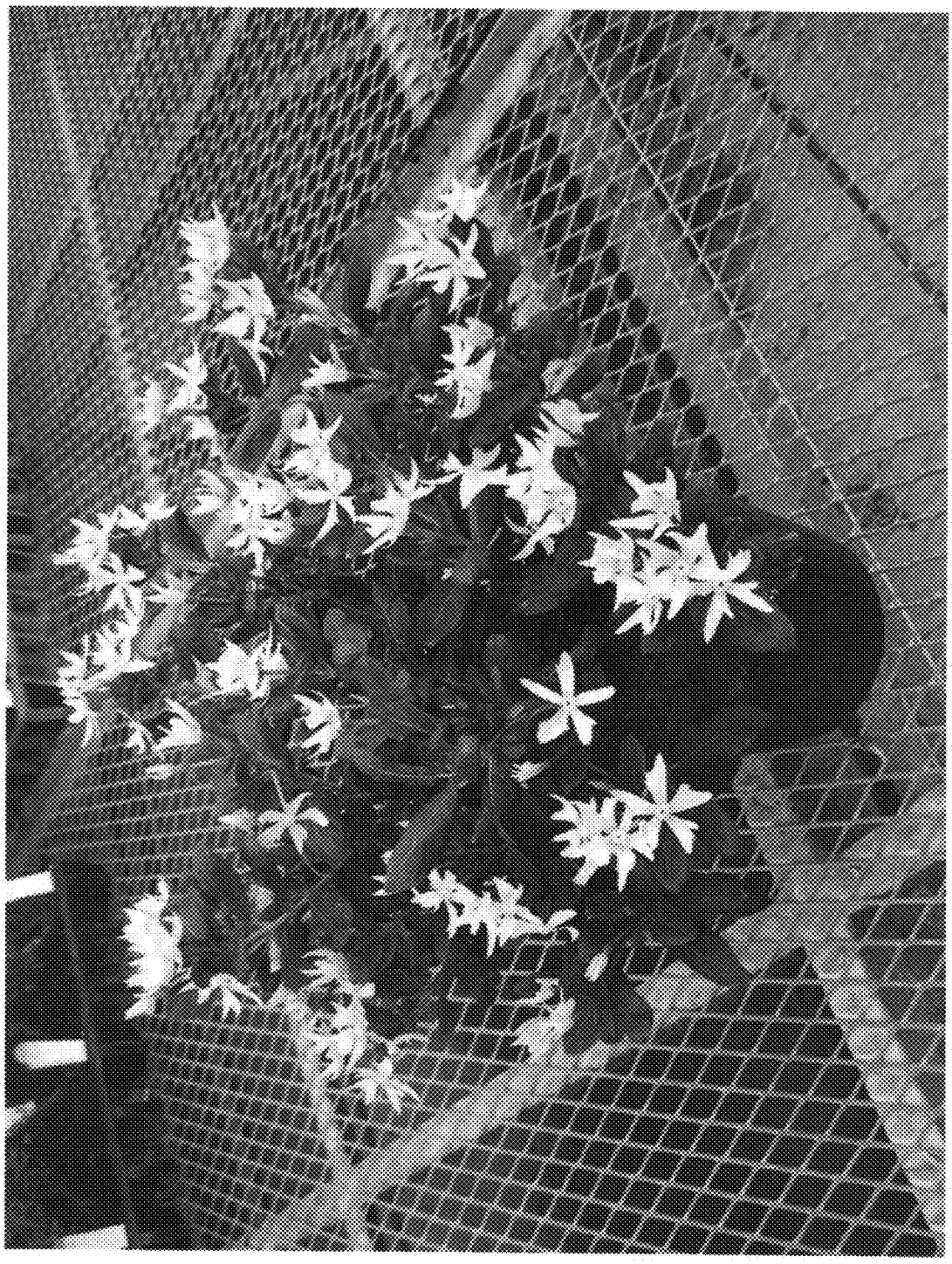

* * * * *